US00PP10039P

United States Patent [19]

Polys

[11] Patent Number: Plant 10,039

[45] Date of Patent: Sep. 23, 1997

[54] CHRYSANTHEMUM PLANT NAMED 'CREAM BLUSH'

[75] Inventor: Susan M. Polys, Salinas, Calif.

[73] Assignee: Yoder Brothers, Inc., Barberton, Ohio

[21] Appl. No.: 605,818

[22] Filed: Feb. 22, 1996

[51] Int. Cl.[6] ..... A01H 5/00

[52] U.S. Cl. ..... Plt./82.2

[58] Field of Search ..... Plt./82.1, 82.2

[56] References Cited

U.S. PATENT DOCUMENTS

| | | | |
|---|---|---|---|
| P.P. 9,441 | 1/1996 | VandenBerg | Plt./82.1 |
| P.P. 9,455 | 2/1996 | Polys | Plt./82.2 |
| 4,616,099 | 10/1986 | Sparkes | 47/58 |

OTHER PUBLICATIONS

Broertjes et al., 1980, "A mutant of a . . . Irradiation of progressive vadiation–induced mutants in a mutation breeding programme with *Chrysanthemum Morifolium*", Euphytica.29:525–530.

Gosling, ed., 1979, "The Chrysanthemum Manual–6th edition", The National Chrysanthemum Society, London, Essex Telegraph Press, Ltd., pp. 329–336.

Broertjes et al, 1978, "Application of Mutation Breeding Methods in the Improvement of Vegetatively Propagated Crops", Elsevier Sci. Pub. Co., New York, pp. 162–175.

Searle, et al., 1968, "Chrysanthemums the Year Round", Blanford Press, London, pp. 27–29, 320–327.

Chan, 1966, "Chrysanthemum and rose mutations induced by X–rays", Am. Soc. Hort. Sci. Proc., pp. 613–620.

Broertjes, 1966, "Mutation breeding of chrysanthemums", Euphytica, 15:156–162.

Dowrick, et al., 1966, "The induction of mutations in chrysanthemum using X– and gamma radiation", Euphytica, 15:204–210.

*Primary Examiner*—Howard J. Locker

*Attorney, Agent, or Firm*—Foley & Lardner

[57] ABSTRACT

A Chrysanthemum plant named Cream Blush particularly characterized by its flat capitulum flat capitulum form; daisy capitulum type; cream-yellow ray floret color; diameter across face of capitulum of 127 to 140 mm when fully opened, when grown as a pinched disbudded pot mum; photoperiodic flowering response of 49 to 55 days after start of short days; plant height, with 20 to 22 long days after sticking unrooted cuttings and with 1 to 2 applications of 2500 ppm B-9 SP ranges from 23 to 28 cm when grown as a pinched pot mum with 4 cuttings in a 15 cm pot; branching pattern is semi-spreading, each plant having 3 to 5 laterals after pinch; and recommended as a disbudded pot mum.

1 Drawing Sheet

The present invention comprises a new and distinct cultivar of Chrysanthemum, botanically known as *Dendranthema grandiflora*, and referred to by the cultivar name Cream Blush.

Cream Blush, identified as 4798 (86-627L02), is a product of a mutation induction program. The new cultivar was discovered and selected by inventor Susan M. Polys on Nov. 25, 1992 in a controlled environment in Salinas, Calif. as one flowering plant within a flowering block established as rooted cuttings from stock plants which had been exposed as unrooted cuttings to an X-ray source of 2000 rads in Fort Myers, Fla. on May 28, 1992. The irradiated parent cultivar was the cultivar White Blush, disclosed in U.S. Plant Application, Ser. No. 08/296,467, now U.S. Plant Pat. No. 9,441, and described as a flat daisy disbud pot mum with a white flower color and a cream-white color of the immature ray florets.

The irradiation program resulting in Cream Blush had as its primary objective the expansion of color ranges of the cultivar Blush, disclosed in U.S. Plant Pat. No. 7,985, and the parent cultivar White Blush. The irradiation program comprised irradiation of cuttings of the parent cultivar at irradiation levels of 1500, 1750 and 2000 rads. A total of 1402 cuttings harvested from a total of 225 irradiated plants were planted on Sep. 21, 1992. Of these, 5 initial selections were made, which selections were then revegetated and reflowered. Three consecutive flowerings resulted in discarding 3 of the original 5 selections on Aug. 3, 1993. The 2 remaining codes were maintained as PIs (Possible Introductions) and further trailed in Salinas, Calif. and Leamington, Ontario, Canada, ultimately resulting in the decision to introduce one selection as Yellow Blush in Oct. of 1994, and one selection as Cream Blush. Yellow Blush is disclosed in U.S. Plant Pat. No. 9,455.

The first act of asexual reproduction of Cream Blush was accomplished when vegetative cuttings were taken from the initial selection in January of 1993 in a controlled environment in Salinas, Calif., by technicians working under supervision of Susan M. Polys.

Horticultural examination of controlled flowerings of successive plantings has shown that the unique combination of characteristics as herein disclosed for Cream Blush are firmly fixed and are retained through successive generations of asexual reproduction.

Cream Blush has not been observed under all possible environmental conditions. The phenotype may vary significantly with variations in environment such as temperature, light intensity and daylength, without, however, any variance in genotype.

The following observations, measurements and comparisons describe plants grown in Salinas, Calif., and in Leamington, Ontario, Canada, under greenhouse conditions which approximate those generally used in commercial greenhouse practice.

The following traits have been repeatedly observed and are determined to be basic characteristics of Cream Blush, which, in combination, distinguish this Chrysanthemum as a new and distinct cultivar:

1. Flat capitulum form.
2. Daisy capitulum type.
3. Cream-yellow ray floret color.
4. Diameter across face of capitulum of 127 to 140 mm when fully opened, when grown as a pinched disbudded pot mum.
5. Photoperiodic flowering response of 49 to 55 days after start of short days.
6. Plant height, with 20 to 22 long days after sticking unrooted cuttings and with 1 to 2 applications of 2500 ppm B-9 SP ranges from 23 to 28 cm when grown as a pinched pot mum with 4 cuttings in a 15 cm pot.

7. Branching pattern is semi-spreading, each plant having 3 to 5 laterals after pinch.

8. Recommended as a disbudded pot mum.

The accompanying photographic drawing is a side view of Cream Blush, grown as a disbudded pot mum with 4 cuttings in a 15 cm pot, with the colors being as nearly true as possible with illustrations of this type.

Of the commercial cultivars known to the inventor, the most similar in comparison to Cream Blush is the parent cultivar White Blush. All traits of Cream Blush are similar to those of White Blush, except for the ray floret color. The ray floret color of Cream Blush is cream-yellow (R.H.S. 9D), while the ray floret color of White Blush is described as white (R.H.S. 155D), with a cream-white color of the immature ray florets (R.H.S. 155A to 1D). Cream Blush differs from its sibling Yellow Blush in ray floret color and flowering response, with Yellow Blush having a 2 to 4 days slower flowering response to short days.

In the following description color references are made to The Royal Horticultural Society Colour Chart. The color values were determined on plant material grown as a pinched pot mum with 4 cuttings in a 15 cm pot in Salinas, Calif. on Mar. 8, 1994.

Classification

*Botanical.*—*Dendranthema grandiflora* cv Cream Blush.

*Commercial.*—Flat daisy disbud pot mum.

INFLORESCENCE

A. Capitulum:

*Form.*—Flat

*Type.*—Daisy.

*Diameter across face.*—127 to 140 mm when fully opened.

B. Corolla of ray florets:

*Color (general tonality from a distance of three meters)* .—Cream yellow.

*Color (upper surface).*—9D.

*Color (under surface).*—10D.

*Shape.*—Straight, pointed, slightly ribbed.

C. Corolla of disc florets:

*Color (mature).*—7B.

*color (mmature).*—144A to 144B.

D. Reproductive organs:

*Androecium.*—Present on disc florets only; scant pollen.

*Gynoecium.*—Present on both ray and disc florets.

PLANT

A. General appearance:

*Height.*—23 to 28 cm when grown as a pinched pot mum with 20 to 22 long days after sticking unrooted cuttings prior to start of short days and with 1 to 2 applications of 2500 ppm B-9 SP.

*Branching pattern.*—Semi-spreading, with 3 to 5 laterals after pinch.

B. Foliage:

*Color (upper surface).*—147A.

*Color (under surface).*—147B.

*Shape.*—Deeply lobed and slightly serrated.

What is claimed is:

1. A new and distinct Chrysanthemum plant named Cream Blush, as described and illustrated.

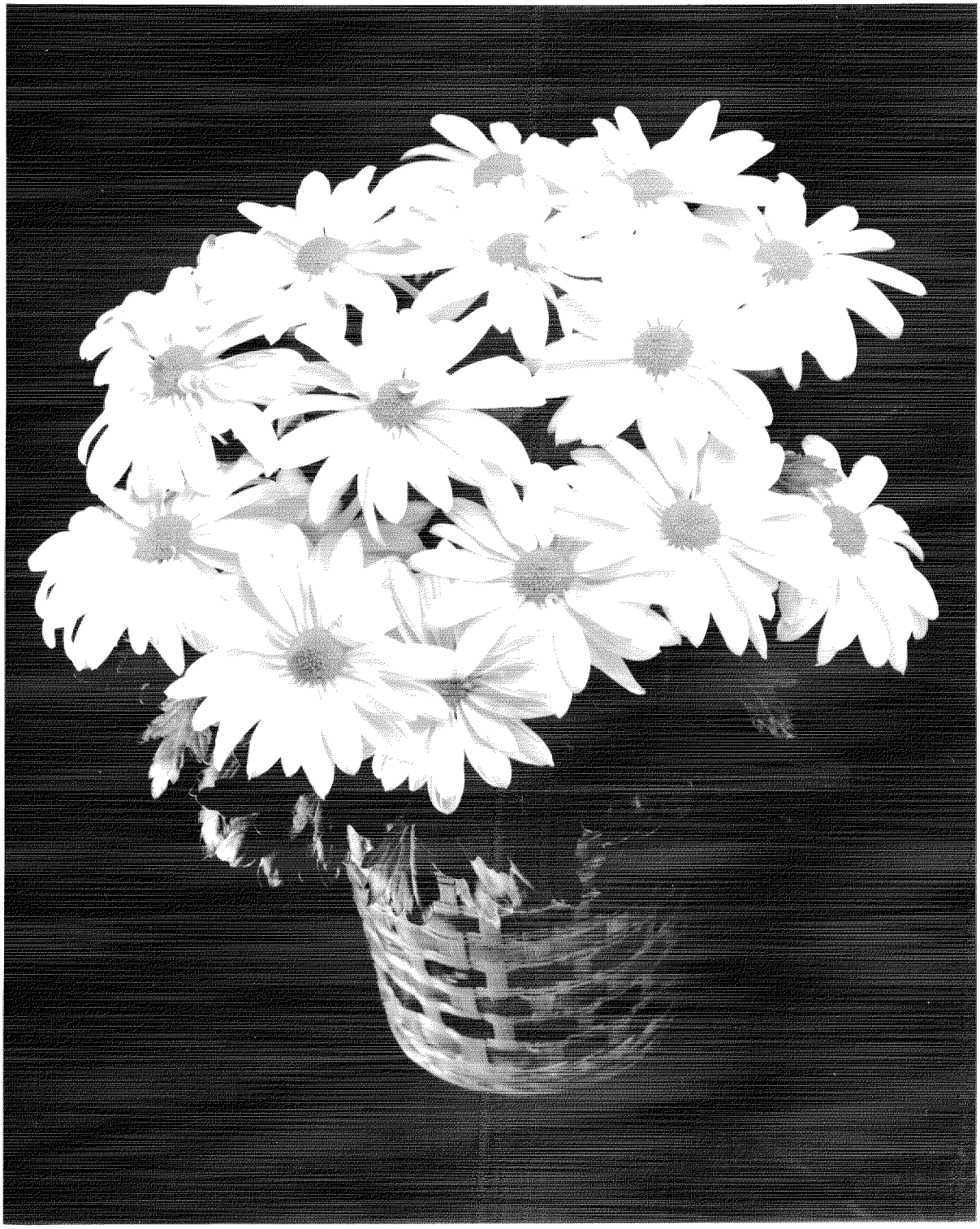

* * * * *